(12) United States Patent
Taskinen et al.

(10) Patent No.: US 9,770,522 B2
(45) Date of Patent: Sep. 26, 2017

(54) CLEANING SYSTEM FOR AN IMAGE PLATE READOUT DEVICE

(71) Applicant: PaloDEx Group Oy, Tuusula (FI)

(72) Inventors: Jari Taskinen, Tuusula (FI); Markus Weber, Espoo (FI); Jarto Luotola, Espoo (FI); Douglas Woods, Franklin, WI (US); Markus Gygax, Zofingen (CH)

(73) Assignee: PaloDEx Group Oy, Tuusula (FI)

( * ) Notice: Subject to any disclaimer, the term of this patent is extended or adjusted under 35 U.S.C. 154(b) by 151 days.

(21) Appl. No.: 14/504,006

(22) Filed: Oct. 1, 2014

(65) Prior Publication Data

US 2015/0056094 A1 Feb. 26, 2015

Related U.S. Application Data

(62) Division of application No. 12/643,605, filed on Dec. 21, 2009, now Pat. No. 8,876,985.

(51) Int. Cl.
*B08B 7/02* (2006.01)
*A61L 2/02* (2006.01)
*A61L 2/025* (2006.01)
*A61L 2/10* (2006.01)
*A61L 2/04* (2006.01)
*A61L 2/08* (2006.01)

(52) U.S. Cl.
CPC ............... *A61L 2/02* (2013.01); *A61L 2/025* (2013.01); *A61L 2/08* (2013.01); *A61L 2/10* (2013.01); *A61L 2/04* (2013.01); *A61L 2/082* (2013.01)

(58) Field of Classification Search
None
See application file for complete search history.

(56) References Cited

U.S. PATENT DOCUMENTS

| 3,495,149 A | 2/1970 | Swain |
| 3,970,844 A | 7/1976 | Fenn et al. |
| 4,096,391 A | 6/1978 | Barnes |
| 4,176,275 A | 11/1979 | Korn et al. |
| 4,236,078 A | 11/1980 | Kotera et al. |
| 4,239,968 A | 12/1980 | Kotera et al. |
| 4,316,666 A | 2/1982 | Ceelen |
| 4,320,296 A | 3/1982 | Ishida et al. |

(Continued)

FOREIGN PATENT DOCUMENTS

| EP | 1640800 | 3/2006 |
| EP | 2128697 | 12/2009 |

(Continued)

OTHER PUBLICATIONS

Communication dated May 7, 2010 and European Search Opinion and European Search Report dated Apr. 28, 2010, received in corresponding European Patent Application No. 09180462.5.

(Continued)

*Primary Examiner* — Eric Golightly
(74) *Attorney, Agent, or Firm* — Andrus Intellectual Property Law, LLP

(57) ABSTRACT

A method of disinfecting a readout device having a reader unit that reads an imaging medium, the method comprising: identifying an absence of the imaging medium from the inside of the readout device; and emitting, from a disinfecting element, radiation capable of destroying disease carriers onto an the interior of the readout device when the imaging medium is absent from inside the readout device.

24 Claims, 1 Drawing Sheet

(56) References Cited

U.S. PATENT DOCUMENTS

| | | |
|---|---|---|
| 4,327,422 A | 4/1982 | Imazeki et al. |
| 4,346,295 A | 8/1982 | Tanaka et al. |
| 4,346,983 A | 8/1982 | Jeromin et al. |
| 4,387,428 A | 6/1983 | Ishida et al. |
| 4,394,581 A | 7/1983 | Takahashi et al. |
| 4,453,162 A | 6/1984 | Money et al. |
| 4,462,113 A | 7/1984 | Iwata |
| 4,472,822 A | 9/1984 | Swift |
| 4,485,302 A | 11/1984 | Tanaka et al. |
| 4,496,973 A | 1/1985 | Horikawa et al. |
| 4,498,005 A | 2/1985 | Oono et al. |
| 4,498,006 A | 2/1985 | Horikawa et al. |
| 4,527,060 A | 7/1985 | Suzuki et al. |
| 4,527,061 A | 7/1985 | Horikawa et al. |
| 4,564,760 A | 1/1986 | Noguchi et al. |
| 4,568,832 A | 2/1986 | Tanaka et al. |
| 4,583,489 A | 4/1986 | Thourson et al. |
| 4,584,483 A | 4/1986 | Kato |
| 4,590,517 A | 5/1986 | Kato et al. |
| 4,710,626 A | 12/1987 | Takahashi et al. |
| 4,739,480 A | 4/1988 | Oono et al. |
| 4,777,597 A | 10/1988 | Shiraishi et al. |
| 4,814,618 A | 3/1989 | Saito et al. |
| 4,816,676 A | 3/1989 | Aagano |
| 4,816,677 A | 3/1989 | Adachi et al. |
| 4,816,690 A | 3/1989 | Adachi et al. |
| 4,877,958 A | 10/1989 | Agano et al. |
| 4,880,987 A | 11/1989 | Hosoi et al. |
| 4,888,695 A | 12/1989 | Shiraishi et al. |
| 4,904,868 A | 2/1990 | Kohda et al. |
| 4,943,723 A | 7/1990 | Adachi et al. |
| 4,960,994 A | 10/1990 | Muller et al. |
| 4,983,834 A | 1/1991 | Lindmayer et al. |
| 5,168,160 A | 12/1992 | Jeromin et al. |
| 5,272,339 A | 12/1993 | Shimura et al. |
| 5,315,444 A | 5/1994 | Ishiguro et al. |
| 5,335,664 A | 8/1994 | Nagashima |
| 5,440,146 A | 8/1995 | Steffen et al. |
| 5,677,940 A | 10/1997 | Suzuki et al. |
| 5,686,882 A | 11/1997 | Giani |
| 5,801,391 A | 9/1998 | Arakawa et al. |
| 5,852,301 A | 12/1998 | Niimura et al. |
| 5,900,640 A | 5/1999 | Ogura |
| 5,923,856 A | 7/1999 | Hazama et al. |
| 5,932,982 A | 8/1999 | Pezzelli, Jr. |
| 5,981,953 A | 11/1999 | Schoeters |
| 6,023,071 A | 2/2000 | Ogura et al. |
| 6,044,131 A | 3/2000 | McEvoy et al. |
| 6,130,440 A | 10/2000 | Ogura |
| 6,236,058 B1 | 5/2001 | Ikami |
| 6,256,405 B1 | 7/2001 | Some et al. |
| 6,315,444 B1 | 11/2001 | Koren |
| 6,376,857 B1 | 4/2002 | Imai |
| 6,469,312 B2 | 10/2002 | Agano |
| 6,528,813 B2 | 3/2003 | Yasuda |
| 6,583,630 B2 | 6/2003 | Mendes et al. |
| 6,680,483 B2 | 1/2004 | Shoji |
| 6,759,673 B2 | 7/2004 | Akimoto et al. |
| 6,936,829 B2 | 8/2005 | Nishioka |
| 7,164,344 B2 | 1/2007 | Deguchi et al. |
| 7,195,645 B2 | 3/2007 | Disilvestro et al. |
| 7,211,818 B2 | 5/2007 | Imai et al |
| 7,227,117 B1 | 6/2007 | Lackemann et al. |
| 7,227,924 B2 | 6/2007 | Zhou et al. |
| 7,245,211 B2 | 7/2007 | Ota |
| 7,308,614 B2 | 12/2007 | Kojori |
| 7,420,197 B2 | 9/2008 | Irisawa |
| 7,492,250 B2 | 2/2009 | Yoshida et al. |
| 7,531,822 B1 | 5/2009 | Minnigh et al. |
| 7,583,930 B2 | 9/2009 | Minotani et al. |
| 7,767,981 B2 | 8/2010 | Kuwabara et al. |
| 7,782,192 B2 | 8/2010 | Jeckelmann et al. |
| 7,889,843 B2 | 2/2011 | Watanabe |
| 7,991,119 B2 | 8/2011 | Yoshida et al. |
| 8,053,737 B2 | 11/2011 | Ohta et al. |
| 8,077,601 B2 | 12/2011 | Maze et al. |
| 2001/0010541 A1 | 8/2001 | Fernandez et al. |
| 2001/0032945 A1 | 10/2001 | Yasuda |
| 2002/0043636 A1 | 4/2002 | Kimura |
| 2002/0060303 A1 | 5/2002 | Yonekawa et al. |
| 2002/0105427 A1 | 8/2002 | Hamamoto et al. |
| 2004/0028174 A1 | 2/2004 | Koren |
| 2004/0066278 A1 | 4/2004 | Hughes et al. |
| 2004/0066279 A1 | 4/2004 | Hughes et al. |
| 2004/0094731 A1 | 5/2004 | Arakawa |
| 2004/0234032 A1 | 11/2004 | Nokita |
| 2005/0078793 A1 | 4/2005 | Ikeda |
| 2005/0218356 A1 | 10/2005 | Apajasaari |
| 2005/0226361 A1 | 10/2005 | Zhou et al. |
| 2005/0247898 A1 | 11/2005 | Yonekawa |
| 2006/0113500 A1 | 6/2006 | Auer et al. |
| 2006/0149167 A1 | 7/2006 | Yeh et al. |
| 2006/0271199 A1 | 11/2006 | Johnson |
| 2007/0086911 A1 | 4/2007 | Yamazaki et al. |
| 2008/0061964 A1 | 3/2008 | Yoshida et al. |
| 2008/0085228 A1 | 4/2008 | Yamazaki et al. |
| 2008/0129486 A1 | 6/2008 | Jeckelmann et al. |
| 2008/0306379 A1 | 12/2008 | Ikuma et al. |
| 2009/0177109 A1 | 7/2009 | Yeh et al. |
| 2009/0302220 A1 | 12/2009 | Micko |
| 2009/0309704 A1 | 12/2009 | Chang et al. |
| 2010/0097830 A1 | 4/2010 | Wang |
| 2010/0191055 A1 | 7/2010 | Minai et al. |

FOREIGN PATENT DOCUMENTS

| | | |
|---|---|---|
| FI | 92633 | 8/1994 |
| JP | 3-6053 | 1/1991 |
| JP | 05225767 | 9/1993 |
| JP | 1152503 | 2/1999 |
| JP | 2002156716 | 5/2002 |
| JP | 2004264609 | 9/2004 |
| JP | 2004283365 | 10/2004 |
| JP | 2005284280 | 10/2005 |
| JP | 2006263609 | 10/2006 |
| JP | 2007097692 | 4/2007 |
| JP | 2007130547 | 5/2007 |
| JP | 2008268837 | 11/2008 |
| JP | 2008301970 | 12/2008 |
| JP | 2004264604 | 9/2009 |
| WO | 2004025366 | 3/2004 |

OTHER PUBLICATIONS

Opposition filed in corresponding European Patent Application No. 09180462.5, dated Apr. 23, 2012.

Communication of a Notice of Opposition received in corresponding European Patent Application No. 09180462.5, dated May 7, 2012.

European Search Report for corresponding application EP 12 19 0509, having a completion date of Nov. 20, 2012.

Notice of Office Action issued in corresponding Korean Patent Application No. 0130132/2009, transmitted Oct. 24, 2013.

Communication from OKABE International Patent Office dated Nov. 22, 2013, referencing Office Action issued in Japanese Patent Application No. 2009-290748.

Notification of Reasons for Refusal issued from Japanese Patent Office on Dec. 26, 2013 in Japanese Application No. 2009-290738.

Office Action for U.S. Appl. No. 12/642,389 date May 2, 2014.

Notice of Reason for Refusal for Japanese Application No. 2009-290748 dated May 13, 2014.

Japanese Office Action in corresponding Japanese Application No. 2015-41115 dated Feb. 25, 2016.

CLEANING SYSTEM FOR AN IMAGE PLATE READOUT DEVICE

CROSS-REFERENCE TO RELATED APPLICATIONS

This application is divisional of U.S. application Ser. No. 12/643,605, filed Dec. 21, 2009, which application was published on Jun. 24, 2010, as U.S. Publication No. U.S. US20100154820 and granted as U.S. Pat. No. 8,876,985 on Nov. 4, 2014, which application claims priority of Finish Patent Application No. 20086240, filed Dec. 23, 2008, which application is incorporated herein by reference.

FIELD OF THE INVENTION

The invention relates to the concept of hygiene, involving for example image plates used in medical imaging processes, and instruments and installations, for example image plate readers, associated therewith. Specifically, the present invention relates to a cleaning system for a set of instruments associated with an image plate readout installation, to a readout device comprising said cleaning system, as well as to a method of cleaning a set of instruments associated with the image plate readout installation.

BACKGROUND OF THE INVENTION

The imaging media employed today in medical imaging processes include a traditional film, a reusable image plate, or an X-radiation monitoring wireless or wired sensor. In the event that a film is used, the film has been accommodated for example in a separate cassette protecting the film from visible light, which cassette may be in contact with a patient and his/her body fluids during radiography. Likewise, the image plate is shielded inside a protection device during radiography, the X-ray image being captured by placing the object to be imaged, for example a patient or part of a patient, between the source of X-radiation and the image plate contained within the protection device. Hence, the image plate protection device may come to contact with a patient and his/her body fluids during an imaging process, such as for example in intraoral radiography, during which the image plate shielded by a protection device is in the patient's mouth.

No matter which of the foregoing imaging media is employed, there is always a risk that disease carriers, originating from a patient and/or medical staff, may migrate to other patients and/or medical staff by way of the imaging medium. In the case of an image plate, for example, the first risk appears as early as in the packaging stage of an image plate, wherein the image plate is inserted for example in a protective cardboard or the like, and then, while accommodated in the protective cardboard or the like, in a shielding device, for example in a sealable hygienic shielding bag, ending up in contact e.g. with a patient during radiography. In the packaging process, an image plate, prior to being inserted in protection devices, may be contaminated e.g. by a packing person, for example by dropping the image plate on the floor or by touching it with bare hands or dirty gloves.

Another risk factor involves the poor liquid tightness of protection devices, for example a shielding bag, whereby, e.g. in intraoral radiography, a patient's body fluids may end up inside the shielding bag and proceed to contaminate an image plate contained in the shielding bag. Another risk with non-liquidproof shielding bags is that disease carriers, possibly inside the shielding bag, may migrate from within the shielding bag into a patient's mouth during radiography.

Still another risk is that the shielding bag is picked up from a patient's mouth for example by a nurse, who then brings the same instruments in contact with other objects, for example readout devices or structural elements or even other shielding bags, whereby disease carriers may pass from the nurse to other protection devices and, in the case of non-liquidproof shielding bags, even all the way to image plates.

There is a still further risk of disease carriers proceeding from an image plate to instruments in close proximity of the image plate, for example to readout device conveyor mechanisms, receiver elements or transfer elements, or to an outlet for image plates, or to a tray into which the read-out image plates return from the readout device, and further thereby to other image plates or persons or elements handling the same.

Prior known are a few solutions for improving the hygiene of, for example, intraoral image plates and instruments and installations associated therewith.

For example, the publication FI 92633 discloses one solution for protecting an intraoral image plate by means of two shielding bags, wherein the image plate is first inserted in an inner shielding bag open at one end, and which inner shielding bag is then inserted into an outer shielding bag, said outer shielding bag being intended to prevent a patient's saliva from proceeding, along with the inner bag, to a readout device, as well as to protect the patient from disease carriers possibly settled on the image plate surface. The image plate can be placed first in a cardboard cover and then in an outer shielding bag. In addition, the publication U.S. Pat. No. 6,315,444 also discloses a solution for protecting an imaging plate by means of an envelope type container, wherein the imaging plate is inserted in the envelope type container by way of a first end of the container for the duration of a radiographic procedure and is removed from a second end of the container after the radiographic procedure.

However, the above-cited solutions involve a few problems, for example a shielding bag opening process with uncontrolled tearing of the shielding bag. This involves a hazard that, in the process of opening a shielding bag, an image plate present inside the shielding bag is dropped, for example, on the floor or some other contaminating surface, whereby disease carriers may end up in contact with the image plate. The envelope type container described in U.S. Pat. No. 6,315,444 is in turn quite complicated in terms of its structure and manufacturing, because therein the point of inserting an image plate into the container is not the same as that of its extraction. Such a container is quite vulnerable to leaks as it includes several openings for the insertion or extraction of an image plate.

Still additionally, the solutions presented in either of the cited publications are not liquid-proof as both are left with a flow-permitting passage in a folded joint established by a foldable flap, which allows a flow of liquid even all the way to contact with an opening intended for the insertion of an image plate, and thence further inside the container and to contact with the image plate. Moreover, for example the envelope type container presented in U.S. Pat. No. 6,315,444 is left with sharp corners as the flap is folded shut. First of all, such sharp corners feel uncomfortable in a patient's mouth, but there is also a hygiene risk as a sharp corner may cause further damage to a patient's mucous membranes and thereby facilitate the transfer of disease carriers to or from the patient's body.

Prior known are also a few solutions for the cleaning of contaminated intraoral image plates. For example, the publication US 2007/0086911 discloses a solution relating to disinfection, wherein the image plate readout device comprises a special disinfecting unit performing the disinfection by means of a thermal treatment, UV radiation, chemicals, or a gas treatment.

A problem in the solution presented in US 2007/0086911 is, however, the fact that the device explicitly disinfects image plates presently contained within an image plate readout device. In the event that a traditional image plate is disinfected for example by means of UV radiation, the image plate must be subjected thereafter to an erasing procedure or at least to a dark treatment prior to its reuse, which claims time and resources with at least one operation added to the process, and secondly, the image plate is not immediately reusable. In addition, powerful UV radiation is harmful to the image plate and shortens its service life.

BRIEF SUMMARY OF THE INVENTION

It is an objective of the invention to set aside drawbacks associated with the prior art. According to one embodiment, the invention pursues to improve the hygiene of image plates used in medical imaging processes, as well as that of instruments and installations, for example image plate readers, involved therein, and thereby to minimize the spreading of disease carriers by way of radiography-related media and/or medical staff amongst patients and/or medical staff members.

The objectives of the invention are achieved by a cleaning system according to claim 1 for a set of instruments associated with an image plate readout device, by a readout device according to claim 9, as well as a cleaning method according to claim 10.

The cleaning system of the invention for a set of instruments associated with an image plate readout device is characterized by what is presented in claim 1 directed to a cleaning system.

The readout device of the invention is characterized by what is presented in claim 9 directed to a readout device.

In addition, the cleaning method of the invention is characterized by what is presented in claim 10 directed to a cleaning method.

The concepts presented in this document are used e.g. in the following meanings: [0019] "The conveyor mechanism" is a mechanism, which conveys or otherwise carries an image plate or a transfer element (either with or without the image plate), inserted in a readout device, at least over part of the way inside the readout device, in order to be read by a reader unit of the readout device. The conveyor mechanism can be a mechanism consisting for example of conveyor belts, a carrier arm, a holder, rollers and/or guides or the like. According to one embodiment, the carrier arm or the image plate holder can be the same as a gripper element serving as the receiver element, the gripper element being adapted not only to receive an image plate or a transfer element, but also to carry the image plate or the transfer element within the readout device. In some embodiments, the conveyor mechanism is also adapted to carry an image plate or a transfer element to an outlet for image plates, which can be a separate outlet or co-function as an inlet, depending on the design of a readout device. [0020] "The receiver element" is for example an element set in the immediate vicinity of a readout device for the reception of an image plate, or a transfer element intended for the image plate, in the readout device. The receiver element can be for example an adapter provided in connection with the conveyor mechanism, enabling image plates or transfer elements for image plates of various sizes to be fed into the readout device. The activation of a receiver element may comprise, for example, activating a set of instruments associated with the inlet of a readout device for enabling the placement of an image plate in said inlet either as such or fitted in a transfer element, for example adjusting an adapter as required by the image plate or the transfer element. According to one embodiment, the adapter may adjust itself for example as required by a transfer element, for example a cassette, in such a way that the transfer element, for example a cassette, remains in the adapter, and an imaging medium present inside the transfer element is passed from the adapter to the readout device for reading, thus also enabling a part of the transfer element remaining in the adapter, as well as the adapter itself, to be disinfected. The activation of a receiver element may also comprise switching the readout device's gripper element to a standby mode, enabling the placement of an image plate in the gripper element either as such or fitted in a transfer element. The receiver element may also be a protective lid of the readout device, which opens upon its activation. [0021] "The transfer element" is for example an element, in which an image plate, used e.g. in intraoral radiography, is carried from place to place. The image plate within said transfer element can be fed into a readout device to be carried by the readout device's conveyor mechanism and further to be read by the readout device's reader elements, and further to an outlet for read-out image plates. The outlet can be a separate outlet or, alternatively, the same as the inlet. The transfer element can be for example an image plate carriage, an adapter, or a cassette relevant to the imaging medium.

According to one embodiment, the cleaning system for a set of instruments associated with an image plate readout device (or in contact with a readout device) comprises a disinfecting element emitting electromagnetic radiation and/or ultrasonic radiation capable of destroying disease carriers. According to this embodiment, the disinfecting element is adapted to emit said radiation towards an image plate conveyor mechanism encompassed by the image plate readout device. The cleaning element is preferably inside the readout device or at least in such a disposition that radiation emitted thereby is not allowed outside the readout device. In one embodiment, the activated mode of a cleaning element is shown by means of providing an indication external of the readout device, for example a signal light and/or an audio signal or an indication by display elements.

According to a second embodiment, the image plate readout device comprises a readout device cleaning system as defined above.

A cleaning system or method, as described in the foregoing, for a set of instruments associated with an image plate readout device (or in contact with a readout device) does indeed offer obvious benefits with respect to the prior art. The cleaning system provides an improvement regarding the hygiene of readout installations by enabling a readout device to be disinfected also on the inside. If, for example, the protection element used to enclose the imaging medium has become damaged for some reason, or if the employed imaging medium or the transfer element associated therewith has become contaminated (for example by a patient's or medical staff member's body fluids and/or by disease carriers), the internal components, for example conveyor elements, of a readout device may also become contaminated by way of such an imaging medium or transfer element. By virtue of the invention, however, the role of a readout device's internal components as a potential source of further contamination can be effectively minimized, because the disinfecting elements enable destroying, among others, disease carriers that have ended up in conveyor mechanisms.

According to one embodiment, the disinfecting element emits radiation also towards receiver elements, which are associated with the readout device and intended for enabling the reception of an image plate and/or a transfer element. The receiver element can be for example an entrance to the readout device for inserting an image plate or a transfer element therein, or it can be a protective lid covering the entrance. Some readout devices may even have several entrances of various sizes for image plates and/or transfer elements of various sizes.

The receiver element can also be an adapter, by means of which for example a cassette is fitted in the entrance of a readout device. The adapter is preferably arranged to fit a cassette in the entrance of a readout device tightly, such that radiation emitted for example by the disinfecting element is not allowed to the environment outside the readout device. In one embodiment, the adapter is a frame, enabling the fitting of varying-size cassettes or image plates or transfer elements of image plates in the entrance of a readout device. In this case, the admittance of radiation to the outside of a readout device is restricted in other ways.

According to one embodiment, the receiver element can also be a gripper element for receiving an image plate or a transfer element.

According to one embodiment, the transfer element, for example a cassette, may remain for example in the entrance of a readout device or in an adapter fitted therein, such that the disinfecting element is capable of emitting radiation towards the entrance or the adapter, and further towards the transfer element, for example a cassette, thus enabling at least part of the transfer element to be disinfected as well. In this case, among others, a part of the cassette can be disinfected for example when the imaging medium has been extracted from the cassette and the cassette is in engagement with the entrance or the adapter.

According to one embodiment, the disinfecting element emits for example UV radiation, X-radiation, thermal radiation and/or ultrasonic radiation. According to one embodiment, while emitting electromagnetic radiation, the disinfecting element can be the same as that used for vacating (erasing) the image plates. According to yet another embodiment, the disinfecting element is only adapted to function when no image plate is present inside the readout device. Among others, this provides the advantage that, if a traditional image plate is disinfected by powerful UV radiation, the image plate must then be subjected to erasing or to a dark treatment before it can be used again.

The operation of a disinfecting element can be adapted to proceed for example as a procedure relevant to image reading, in a timed fashion, or as an independent procedure.

It should also be noted that, according to one embodiment for improving the hygiene of a readout device, the internal and/or external surfaces of the readout device, particularly those in contact with an image plate or otherwise subject to repeated touching, can also be coated with a so-called antimicrobiological material. According to one embodiment, a specific part of the readout device can also be manufactured from an antimicrobiological material. Such antimicrobiological material can be for example a material included in the SAME group (self-assembling monolayer end groups)

DESCRIPTION OF THE FIGURES

Preferred embodiments of the invention will be described in the next section in slightly more detail with reference to the accompanying figures, in which.

DETAILED DESCRIPTION OF THE SEVERAL VIEW OF THE DRAWINGS

Figure 1A:
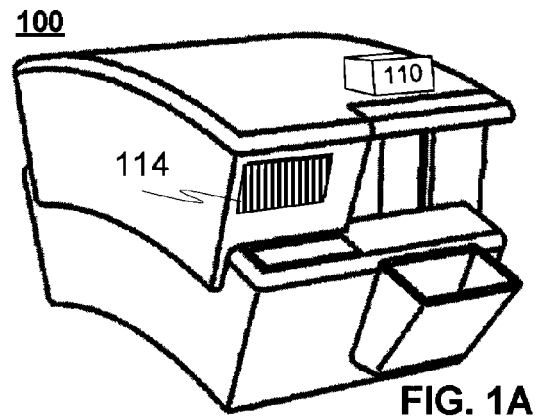
FIGS. 1A-1C show one exemplary image plate readout device and a cleaning system for instruments relevant thereto.
Figure 1B:
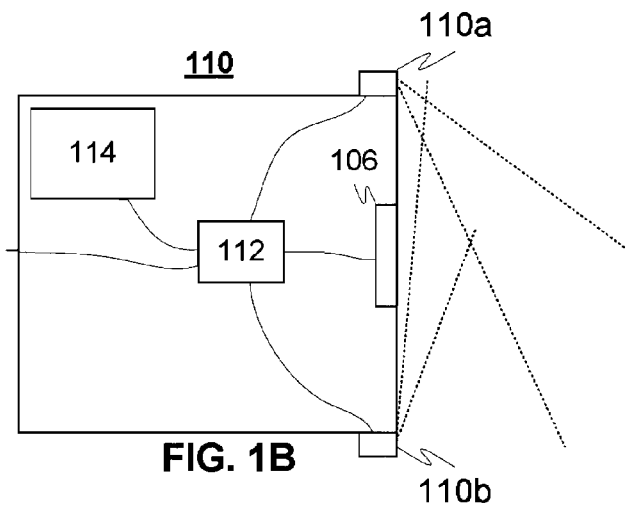
Figure 1C:
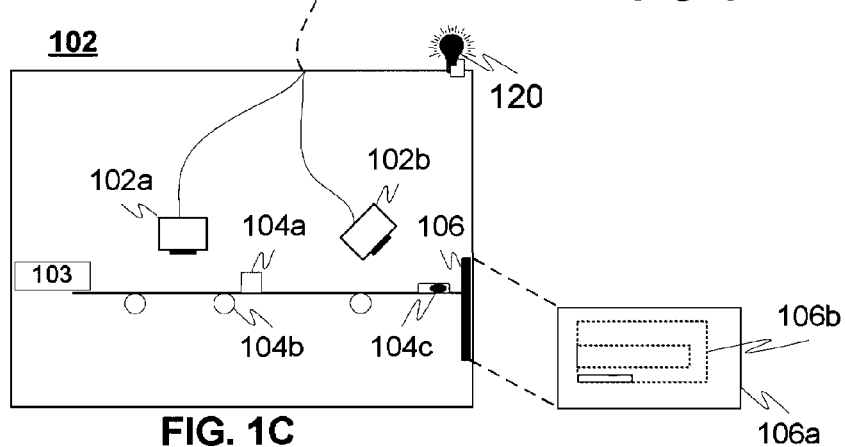

FIG. 1A shows one exemplary image plate readout device 100 and FIG. 1C a cleaning system 102 for instruments associated or in contact therewith. According to one embodiment, the cleaning system 102 comprises a disinfecting element 102a, which emits electromagnetic radiation and/or ultrasonic radiation destroying disease carriers and which is adapted to emit said radiation towards an image plate conveyor mechanism 104a, 104b, 104c encompassed by the image plate readout device. The conveyor mechanism is for example a carrier arm or some other image plate holder 104a, a roller or guide 104b, which is adapted to convey or at least to displace or guide an image plate or a transfer element within the readout device. The conveyor mechanism can also be a gripper element 104c.

The disinfecting element 102a, 102b can be adapted to emit radiation also towards receiver elements 106, which are associated with the readout device 100 and intended for enabling the reception of an image plate and/or a transfer element, for example towards an entrance 106a and/or an adapter 106b intended for the reception of an image plate or a transfer element, or towards a protective lid in engagement with an entrance to the readout device. According to one embodiment, the readout device 100 may comprise several cleaning elements 102a, 102b or, alternatively, a single cleaning element 102a can be adapted to be pivotable or otherwise movable, such that a beam of radiation emitted by the disinfecting element can be directed as desired either towards the conveyor elements only, towards the receiver elements, or optionally towards both.

According to one embodiment, the disinfecting element 102a used for disinfection (especially in the embodiment with the disinfecting element emitting electromagnetic radiation) can be the same element as that used for vacating or erasing the image plates.

According to one embodiment, the cleaning element may comprise identification means 103, which identify the presence of an image plate inside the readout device, and wherein the identification means 103 are adapted to restrict the disinfecting elements 102a, 102b to only function when no image plate is present inside the readout device. This enables, for example, the disinfection of elements intended for conveying an image plate, as well as image plate transfer elements (sans the image plate) and image plate receiver elements, without exposing the image plate to radiation, for example UV radiation.

According to one embodiment, in communication with the image plate readout device is arranged a detection element 110 for detecting an object, for example a user, or a gesture or motion performed by the user. The detection element is preferably set in data communication with the readout device such that, upon detecting an object for example in the proximity of the readout device, the detection element is adapted to communicate a signal to the readout device or to control elements 112. According to one embodiment, the control elements are in turn adapted, upon being triggered by a signal communicated by the detection element, to perform some function, for example to control the operation of a disinfecting element for example as a procedure relevant to image reading, in a timed fashion, or as an independent procedure.

The detection element 110a, 110b can be for example a camera or a radar with an ability to observe gestures or motions performed by a user, for example on the basis of pattern recognition. In this case, the control unit 112 is adapted to interpret the gestures or motions performed by a user and to control a procedure relevant to the detected gesture, for example to activate the cleaning system's cleaning elements 102a, 102b either immediately or with a delay. FIG. 1B shows also a means indicative of an active mode of the cleaning element, which in this case is a signal light 120. According to one embodiment, an indication about the active mode of a cleaning element can also be given through the intermediary of a guidelining element 114.

It should be noted, however, that the readout device cleaning system of the invention can also be implemented without the detection instrumentation depicted in FIG. 1B. In this case, the control element 112, which control, among others, the cleaning elements, is disposed elsewhere in communication with the readout device, for example in communication with the cleaning system 102.

Described above are but a few embodiments for a solution of the invention. The principle of the invention is naturally subject to variations within the scope of protection defined by the claims, regarding, for example, implementation details as well as application sectors. Although the above description deals quite specifically with intraoral image plates and equipment and elements relevant to reading or processing the same, the invention is not limited to these, the intraoral image plate being just one example of image plates commonly used in radiography.

It should also be noted that the equipment and instruments shown in the figures are not necessarily to scale in all aspects thereof, and that for example the image plates and/or the transfer elements encompassing an image plate can be fed into the readout device also in vertical plane, even though, for example in FIG. 1C, an adapter 106b is depicted in horizontal plane.

The invention claimed is:

1. A method of disinfecting a readout device having a reader unit that reads an imaging medium, the method comprising:
   conveying with a conveyor mechanism the imaging medium to and from the reader unit inside the readout device;
   identifying an absence of the imaging medium inside the readout device;
   emitting, from a disinfecting element, radiation capable of destroying disease carriers onto the conveyor mechanism and an interior of the readout device when the imaging medium is absent from inside the readout device.

2. The method according to claim 1, comprising receiving, with a receiver element associated with the readout device, a transfer element configured to receive the imaging medium; conveying the transfer element and the imaging medium with the conveyor or mechanism, and
   when the imaging medium is absent from the readout device, emitting the radiation onto the receiver element.

3. The method according to claim 2, comprising enabling at least one of image plate media having different sizes, respectively, and transfer elements having different sizes, respectively, to be fed into the readout device.

4. The method according to claim 1, wherein the disinfecting element is one of a plurality of cleaning units.

5. The method according to claim 4, comprising emitting radiation from one cleaning unit in the plurality of cleaning units towards the conveyor mechanism and comprising emitting radiation from another cleaning unit in the plurality of cleaning units towards a receiver element configured to receive the imaging medium.

6. The method according to claim 1, comprising subsequently emitting radiation from the disinfecting element that erases the imaging medium.

7. The method according to claim 1, comprising detecting an object of detection outside of the readout device and then communicating a signal to the control element; wherein the control element is triggered by the signal to cause the disinfecting element to perform a function.

8. The method according to claim 7, wherein the function is emitting radiation.

9. The method according to claim 7, wherein the function is controlling emission of radiation.

10. The method according to claim 7, wherein the object of detection is a pattern of movement.

11. The method according to claim 1, comprising indicating an active mode of the cleaning element to a user.

12. The method according to claim 11, comprising indicating the active mode of the cleaning element via a signal light.

13. The method according to claim 1, wherein the radiation is selected from the group consisting of electromagnetic radiation and ultrasonic radiation.

14. The method according to claim 1, comprising displacing or guiding of the imaging medium through the readout device.

15. The method according to claim 1, further comprising:
   detecting an object of detection outside of the readout device; and
   communicating a signal to a control element;
   wherein the control element is triggered by the signal to cause the disinfecting element to control emission of radiation.

16. The method according to claim 15, wherein the object of detection is a pattern of movement.

17. The method according to claim 1, wherein at least a portion of the readout device is constructed of an antimicrobial material selected from the self-assembling monolayer end (SAME) group.

18. A method of disinfecting a readout device having a reader unit that reads an imaging medium, the method comprising:
   identifying an absence of the imaging medium from the inside of the readout device; and
   emitting, from a disinfecting element, radiation capable of destroying disease carriers onto an interior of the readout device when the imaging medium is absent from inside the readout device.

19. The method of claim 18, further comprising directing the radiation from the disinfecting element towards at least one of a conveyor mechanism, a transfer element or a receiver element within the readout device.

20. The method of claim 19, wherein the disinfecting element comprises a first disinfecting element and a second disinfecting element, the first disinfecting element emits radiation directed towards the conveyor mechanism and the second disinfecting element emits radiation directed towards the receiver element.

21. The method of claim 19, further comprising:
   directing radiation from the disinfecting element towards one of the conveyor mechanism or the receiver element;
   moving the disinfecting element; and directing radiation from the disinfecting element towards the other of the conveyor mechanism or the receiver element.

22. The method according to claim 18, wherein the radiation emitted from the disinfecting element comprises at least one of: UV radiation, X-radiation, thermal radiation, electromagnetic radiation and ultrasonic radiation.

23. The method according to claim 18, further comprising:
   identifying a presence of the imaging medium inside of the readout device; and
   emitting radiation from the disinfecting element towards the imaging medium to vacate the imaging medium.

24. The method according to claim 18, further comprising providing an indication external of the readout device while emitting radiation from the disinfecting element.

\* \* \* \* \*